United States Patent [19]

Dean

[11] Patent Number: 4,614,776

[45] Date of Patent: Sep. 30, 1986

[54] POLYMERIZATION INITIATOR

[75] Inventor: Barry D. Dean, Broomall, Pa.

[73] Assignee: Atlantic Richfield Company, Los Angeles, Calif.

[21] Appl. No.: 826,395

[22] Filed: Feb. 5, 1986

Related U.S. Application Data

[62] Division of Ser. No. 759,771, Jul. 29, 1985, which is a division of Ser. No. 668,059, Nov. 5, 1984, Pat. No. 4,556,512.

[51] Int. Cl.$^4$ .............................................. C08F 4/04
[52] U.S. Cl. .................................................. 526/204
[58] Field of Search ........................................ 526/204

[56] References Cited

U.S. PATENT DOCUMENTS 3,957,750  5/1976  MacLeay ........................... 526/204

Primary Examiner—Harry Wong, Jr.
Attorney, Agent, or Firm—Dennis M. Kozak

[57] ABSTRACT

[2,5,8,11]-tetraalkyl-[2,5,8,11]-tetracyano-cis-6a′ carboxy, 12a′ oxoacide-3,4:9,10 bisdiazobicyclooctane compounds are disclosed. In one embodiment, the compounds are capable of initiating free radical polymerization and are well suited for the preparation of polymers having block type structures.

1 Claim, No Drawings

POLYMERIZATION INITIATOR

This is a division of application Ser. No. 06/759,771 filed July 29, 1985, which is a division of U.S. Ser. No. 06/668,059, filed Nov. 5, 1984, now U.S. Pat. No. 4,556,512 issued Dec. 3, 1985.

This invention relates to polymerization.

More specifically, this invention relates to a novel type of azo initiator capable of initiating free radical polymerization.

In one of its more specific aspects, the azo initiator of this invention, in addition to initiating free radical polymerization, is capable of reacting with a hydroxyl, amine or mercapto terminated polymer.

The use of initiators to start the polymerization of monomers is well known. The multifunctionality of the initiators of this invention, which allow both free radical polymerization to occur as well as condensation type reactions, makes the initiators of this invention particularly well suited for the preparation of polymers comprised of radial block type structures.

According to this invention, there is provided a compound having the formula:

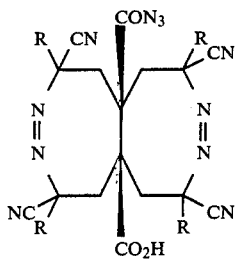

wherein each R separately represents a methyl or ethyl moeity.

The chemical name of the above compound is [2,5,8,11]-tetraalkyl-[2,5,8,11]-tetracyano-cis 6a' carboxy, 12a' oxoazide-3,4:9,10 bisdiazo bicyclooctane.

The above compound, which is the initiator of the invention, is prepared according to the following reaction sequence in which each R separately represents a methyl or ethyl moiety:

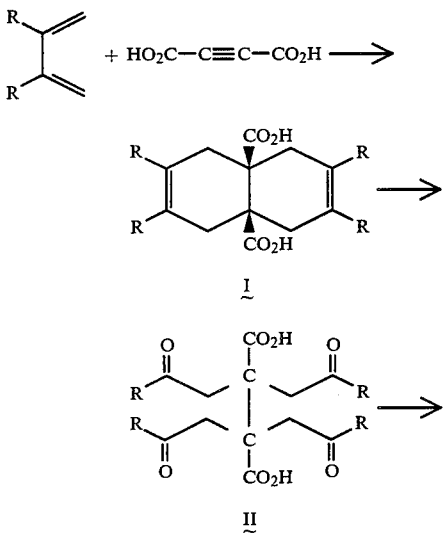

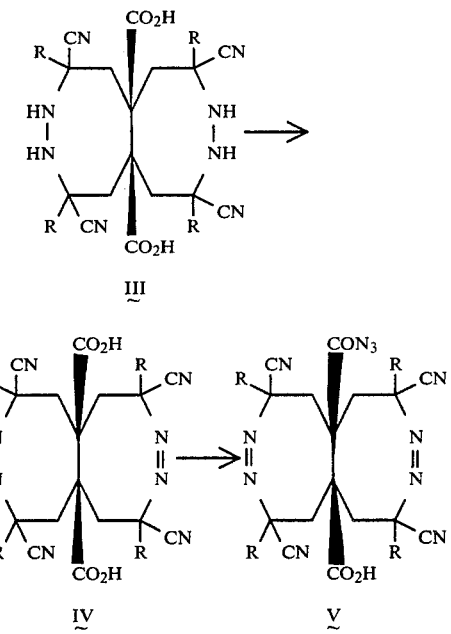

Also, according to this invention there is provided the compound represented by Structure III. The chemical name of this compound is [2,5,8,11]-tetralkyl-[2,5,8,11]-tetracyano-cis-6a',12a' dicarboxy-3,4:9,10 bishydrazobicyclooctane.

According to this invention there is also provided the compound represented by Structure IV. The chemical name of this compound is [2,5,8,11]-tetralkly-[2,5,8,11]-tetracyano-cis-6a',12a' dicarboxy-3,4:9,10 bisdiazobicyclooctane.

The following examples demonstrate the preparation of the compounds identified in Structures I through V.

EXAMPLE 1

This example demonstrates the preparation of the compound represented by Structure I.

Acetylene dicarboxylic acid (22.8 grams, 0.20 mole) and 2,3-dimethyl-1,3-butadiene (32.9 grams, 0.40 mole) were dissolved in 75 milliliters of a (60:40) chlorobenzene/dimethylformamide solution.

Zinc chloride (1 mole % based on the amount of the acetylene dicarboxylic acid) was added to the above solution and the reaction mixture was heated to 87° C. and held there for eight hours.

Partial precipitation of the product occurred during the Diels-Alder reaction. The reaction mixture was chilled (0°–5° C.) and about 120 milliliters of hexane was added to the mixture which resulted in the precipitation of the remaining cyclo addition product.

The Diels-Alder adduct product (identified as Structure I; R=methyl) was recovered as a fine white powder (50.5 grams; 91% yield) having a melting point range of 137°–141.5° C.

The carboxylic acid content (as determined by KOH/pyridine titration) was two equivalents/mole. Elemental analysis (calculated) for the white powder product was C:69.04%, H:7.96% and O:22.99%. Elemental analysis (found) was C:69.11%, H:7.98% and O:22.91%.

EXAMPLE 2

This example demonstrates the preparation of the compound represented by Structure II.

About 25 grams (0.089 mole) of the Structure I, Diels-Alder adduct product prepared according to the procedure of Example 1, were dissolved in a two phase mixture of chlorobenzene (50 grams) and water (50 grams, ph=7.4).

Sodium periodate (10 grams), potassium permanganate (0.45 gram) and tetrahexyl ammonium iodide (1.0 gram) were added and dissolved in the aqueous phase.

Next, a Lemieux-Von Rudloff oxidation was carried out at 25° C. for 22 hours and the residual oxidizing agent was destroyed with the addition of 2.5 grams of sodium hydrogen sulfite.

The organic layer (off yellow color) was separated and dried over 3.0 grams of magnesium sulfate. The drying agent was filtered and the chlorobenzene solvent was removed under vacuum (0.5 mm/40° C.).

The product which remained (Structure II; R=methyl) was a pale yellow oil (30.6 grams, 100% yield). The elemental analysis, the $^1$H NMR and the $^{13}$C NMR data obtained for the Structure II product are summarized below in Table I.

TABLE I
Analysis and Data for the Compound of Structure II

| Elemental Analysis: | carbon | hydrogen | oxygen |
|---|---|---|---|
| Calculated (%) | 56.14 | 6.47 | 37.37 |
| Found (%) | 56.58 | 6.52 | 36.91 |

$^1$H NMR (δ, CDCl$_3$):

2.15, single-broad, 12H 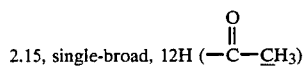

2.64, broadened singlet, 8H (—C—C$\underline{H}_2$—)

10.8, broad singlet, 2H (D$_2$O exchangeable)

$^{13}$C NMR (decoupled, ppm, CDCl$_3$):

27.5 (—$\underline{C}$—CO$_2$H)

29.5 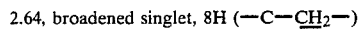

40.5 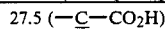

179 (—$\underline{C}$O$_2$H)

208 

EXAMPLE 3

This example demonstrates the preparation of two of the compounds of this invention represented by Structures III and IV.

About (30.6 grams (0.089 mole) of the oxidized Diels-Alder adduct product (Structure II) prepared according to the procedure of Example 2, were dissolved in aqueous tetrahydrofuran (40% water) and neutralized with two equivalents of 50° C. triethylamine (18 grams, 0.178 mole).

The resulting solution was added to a 500 milliliter aqueous soltuion of sodium cyanide (17.5 grams, 0.357 mole) and hydrazine sulfate (23.14 grams, 0.178 mole).

The resulting solution was stirred for 3 hours at 45° C., then cooled to room temperature. The reaction solution was then acidified (to litmus) with 1% aqueous hydrochloric acid solution.

A sample aliquot was taken and extracted with diethylether. The ethereal layer was dried over magnesium sulfate, filtered and the diethylether was removed under vacuum.

An off white powder product was isolated (m.p. 101° C.), analyzed and identified as having the general formula of Structure III (R=methyl). Elemental analysis data of the product are summarized below.

| | carbon | hydrogen | nitrogen | oxygen |
|---|---|---|---|---|
| Calculated (%) | 54.28 | 5.92 | 25.32 | 14.46 |
| Found (%) | 54.97 | 6.00 | 25.12 | 14.79 |

The remaining acidified reaction solvent was cooled to 5° C. in an ice bath and treated, dropwise, with a bromine/carbontetrachloride solution (18% Br$_2$, 10 g) over 20 minutes. Excess bromine was destroyed with 5 grams of sodium hydrogen sulfite.

A white solid was isolated after extraction with diethyl ether, drying with magnesium sulfate and removal of the ethereal solvent.

The solid product was washed extensively (5×200 ml) with cold (5° C.) water, then dried in a vacuum desicator over calcium sulfate.

The white solid was recovered (28.6 grams, 73% yield) and was found to have a melting point of 132° C. (decomposition). Structure assignment (Structure IV) was made based on $^1$H NMR, $^{13}$C NMR and $^{15}$N NMR data set forth in Table II.

TABLE II
Compound NMR Data of Structure IV $^1$H NMR (δ, CDCl$_3$):

1.45, singlet, 12H (—C$\underline{H}_3$)

1.8, doublet, 4H, J = 4Hz Geminal
1.9, doublet, 4H, J = 4Hz —CH$_2$—
11.2, singlet, 2H, D$_2$O exchangeable $^{13}$C NMR (decoupled, ppm, CDCl$_3$):

12.5 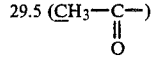

27.5 (—$\underline{C}$—CO$_2$H)

28.5 (C$\underline{H}_2$—)

53.6 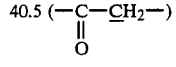

122 (—$\underline{C}$≡N)

181 (—$\underline{C}$O$_2$H)

$^{15}$N NMR (ppm, CH$_3$NO$_2$ relative):

−122.21 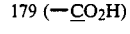

136.58 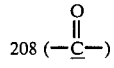

EXAMPLE 4

This example demonstrates the preparation of the initiator of this invention represented by Structure V with each R representing methyl moiety.

About 28.6 grams (0.065 mole) of the bicyclic azo compound of Structure IV, prepared using the procedure of Example 3 were dissolved in 200 ml of a mixture of tetrahydrofuran:water (2:1 vol/vol).

The resulting solution was cooled to 0° C. in a ice-/sodium chloride/water bath and triethylamine (13.1 grams, 0.180 mole) in 50 milliliters of tetrahydrofuran was added to the solution.

The reaction mixture was cooled to −20° C. with a dry ice/acetone slurry and a solution of ethyl chloroformate (3.51 grams, 0.032 mole) in 50 milliliters of tetrahydrofuran was added to the reaction mixture over 20 minutes.

The reaction mixture was stirred at −20° C. for one hour and a solution of sodium azide (2.2 grams, 0.032 mole) in 100 milliliters of water was added over a one hour period.

The reaction mixture was allowed to warm to −5° C. and stirred again for one hour.

The reaction mixture was diluted with 1.5 volumes of water resulting in the precipitation of a pale yellow powder. The powder was purified by dissolving it in chloroform and precipitating with excess petroleum ether.

The pale yellow powder (20.3 grams, 70% yield) was found to have a melting point of 77° C. (decomposition) and was analyzed by infrared, $^1$H NMR, $^{13}$C NMR and $^{15}$N NMR spectroscopy. On the basis of the following spectral data set forth in Table III, Structure V, [2,5,8,11]-tetramethyl-[2,5,8,11]-tetracyano-cis-6a′ carboxy, 12a′ oxoazide-3,4:9,10 bisdiazobicyclooctane, was assigned to the product.

| Infrared (CM$^{-1}$, CHCl$_3$): | 1687 (—C(=O)—N$_3$) |
|---|---|
| $^1$H NMR (δ, CDCl$_3$): | 1.45, singlet 12H |
| | 1.8, doublet × doublet, 4H J = 4.5Hz |
| | 1.88, doublet × doublet, J = 4.5Hz |
| | 11.0, singlet, 1H, D$_2$O exchangeable |
| $^{13}$C NMR (decoupled, ppm, CDCl$_3$) | |
| 12.5 (N≡C—$\underline{C}$—CH$_3$) | |
| 28.8 (—$\underline{C}$—CO$_2$H) | |
| 30.1 (—$\underline{C}$—CON$_3$) | |
| 28.1, 29.5 (—CH$_2$—) | |
| 53.7 (—$\underline{C}$(CH$_3$)—C≡N) | |
| 122.2 (—$\underline{C}$≡N) | |
| 162.3 (—$\underline{C}$(=O)—N$_3$) | |
| 180.2 (—$\underline{C}$(=O)—OH) | |
| $^{15}$N NMR (ppm, CH$_3$NO$_2$ relative) | |
| a −233 | |
| b −138  —C(=O)—N=N=N | |
| c −133           a  b  c | |
| −122.2 (—C≡$\underline{N}$) | |
| 136.7 (—$\underline{N}$=$\underline{N}$—) | |

Structure V, the bisdiazobicyclooctane initiator of this invention consists of two azo linkages which can be thermally activated to form radical species which will initiate the free radical polymerization of any suitable free radical polymerizable monomer. And the γ-carboxy carbonylazide moiety will undergo a condensation reaction with one hydroxyl, amine or mercapto terminated polymer. Accordingly, the compound of Structure V is suitable for use as a polymerization initiator and as such is capable of producing radial block polymers having up to five arms, four of which can be identical.

It will be evident from the foregoing that various modifications can be made to this invention. Such, however, are considered as being within the scope of the invention.

What is claimed is:

1. A method for starting the polymerization of at least one free radical polymerizable monomer which comprises incorporating into said monomer an effective amount of an initiator having the formula wherein each R separately represents a methyl or ethyl moiety, to initiate polymerization of the said at least one monomer.

* * * * *